United States Patent [19]

Doyle et al.

[11] Patent Number: 5,709,660
[45] Date of Patent: Jan. 20, 1998

[54] NEEDLE EXTRACTOR

[76] Inventors: Patricia A. Doyle, 63 Short St.; Joseph Grisanzio, 122 Ashley La., both of Middleboro, Mass. 02346

[21] Appl. No.: 637,094

[22] Filed: Apr. 24, 1996

Related U.S. Application Data

[63] Continuation-in-part of Ser. No. 297,105, Aug. 29, 1994, abandoned.

[51] Int. Cl.[6] .................................................. A61M 5/00
[52] U.S. Cl. .......................... 604/116; 604/117; 604/175; 29/268; 254/21
[58] Field of Search .............................. 606/131, 138, 606/147, 205–210; 604/116, 117, 175; 81/418, 419, 426, 426.5; 29/268; 254/21, 22, 27

[56] References Cited

U.S. PATENT DOCUMENTS

| | | | |
|---|---|---|---|
| 478,009 | 6/1892 | Hollis | 81/419 |
| 617,247 | 1/1899 | Gholson | 606/208 |
| 949,905 | 2/1910 | Knur, Jr. | 29/268 |
| 1,781,419 | 11/1930 | Wallace | 81/426 |
| 2,215,662 | 9/1940 | Generes | 29/268 |
| 3,357,085 | 12/1967 | Martin | 29/268 X |
| 3,540,106 | 11/1970 | Goldman | 29/268 |
| 4,491,135 | 1/1985 | Klein | 606/147 |
| 4,571,808 | 2/1986 | King | 81/302 X |
| 4,640,274 | 2/1987 | Nakamoto | 128/321 |
| 4,658,489 | 4/1987 | Johnston | 29/268 |
| 5,077,879 | 1/1992 | Haviv | 29/268 |
| 5,246,449 | 9/1993 | Webster | 606/131 |
| 5,460,612 | 10/1995 | Madore | 604/116 |

*Primary Examiner*—Robert A. Hafer
*Assistant Examiner*—Justine R. Yu
*Attorney, Agent, or Firm*—Hamilton, Brook, Smith & Reynolds, P.C.

[57] ABSTRACT

A needle extractor is provided which has top and bottom members which include top and bottom blades for inserting between a shank portion of a needle assembly and a patient's skin surface. The top blade has a longitudinal gutter or channel for positioning and aligning the shank portion of the needle assembly and a vertical finger projection with a notch for retaining tubing coupled to the needle assembly. The blades have a common slot for receiving a needle portion of the needle assembly. Each member also has a handle for gripping the extractor. The top member is pivotally attached to the bottom member such that when the blades, being generally disposed parallel to each other and substantially overlapping, are inserted between the shank portion and the skin surface, and the top blade is pivoted relative to the bottom blade, the needle assembly is removed from the skin surface.

20 Claims, 7 Drawing Sheets

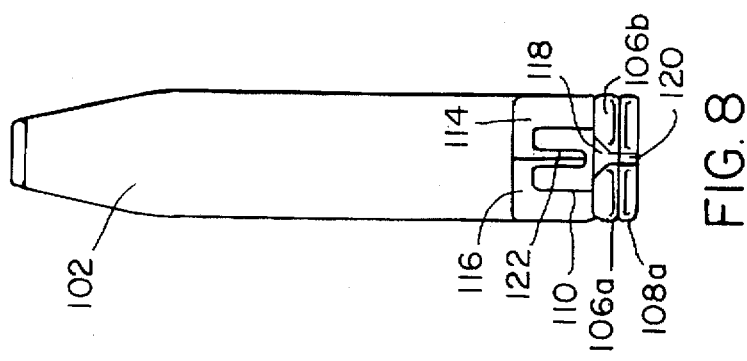
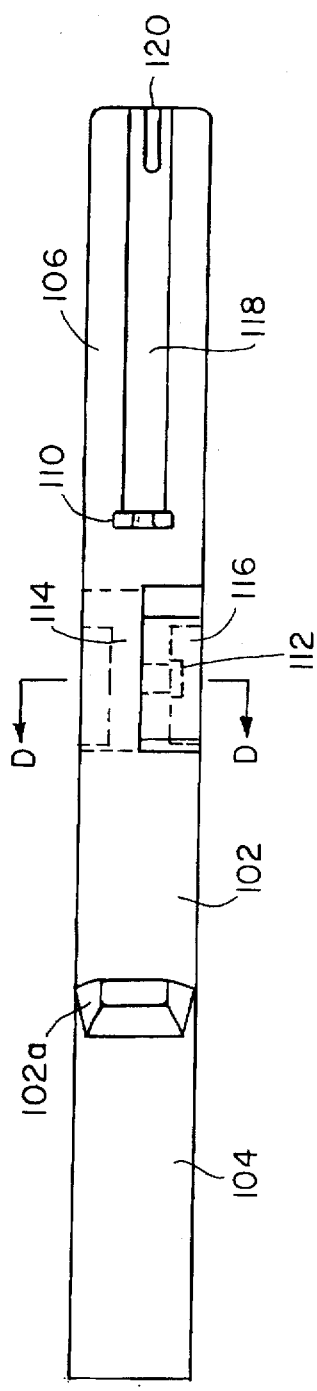
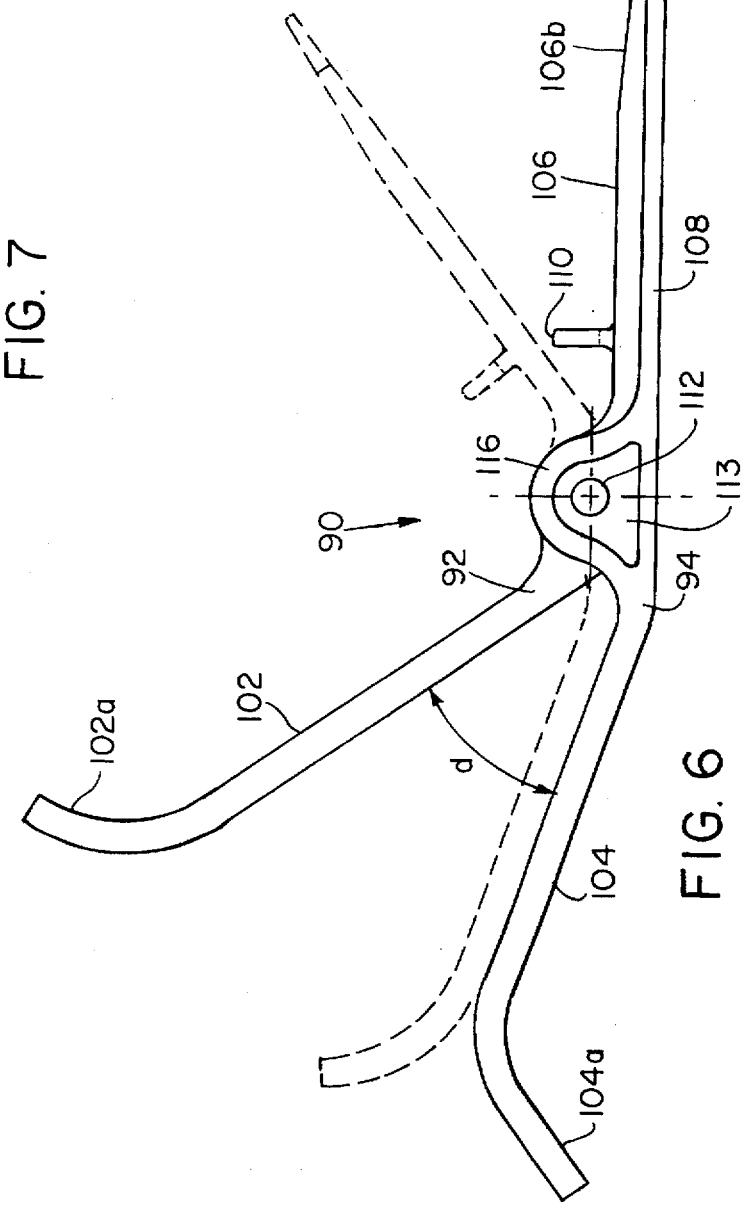

NEEDLE EXTRACTOR

RELATED APPLICATION

This is a continuation-in-part of U.S. patent application Ser. No. 08/297,105 filed Aug. 29, 1994, now abandoned, which is incorporated herein by reference in its entirety.

BACKGROUND OF THE INVENTION

Many medical patients that have communicable infectious disease processes which are blood borne pathogens require multiple daily medications which must be administered intravenously. To provide caregivers direct access to blood vessels large enough to administer medications, these patients are usually given an infusion aid known as a "port". One end of the port is inserted into a large blood vessel and the other end is surgically anchored beneath the patient's skin.

To access the port, the caregiver inserts a needle through the skin overlaying the port and into the port itself. The port is surgically implanted under the skin, usually, but not necessarily restricted to, the chest wall area (similar to implanting a cardiac pacemaker). To access this kind of port, a caregiver typically uses a specially designed 90 degree "right angle" needle assembly. For example, FIG. 1 shows a right angle needle assembly 10 inserted through a skin surface 50 of subcutaneous tissue layer 52 into a port 20. The needle assembly 10 comprises a needle portion 14 coupled to the proximate end of a shank portion 12, the shank portion 12 being disposed generally parallel to the skin surface 50. A tubing 16 for delivery of medication from a source is coupled to the distal end of the shank portion 12. The port 20 is positioned below the skin surface 50 and secured to an underlying muscle layer 56 by sutures 54. A catheter 30 is coupled between a stem 22 of port 20 and a blood vessel 40.

A right angle needle assembly is typically changed at least weekly to prevent infection from occurring at the site of insertion and within the port itself. To remove the needle from the port without injuring the tissue surrounding the port or dislodging the port from the blood vessel to which it is coupled, the caregiver must apply firm pressure with one hand on the skin surface overlaying the port itself while removing the needle with the other hand. This process places the caregiver at substantial risk of receiving an accidental puncture from the extracted needle. This situation is particularly dangerous because of the high probability of the needle being contaminated with a blood borne pathogen carried by the patient.

The moment of highest risk occurs when the needle has exited the port and there is no further need to exert the full force initially required in extracting the needle. As a result, the caregiver has a significant tendency to overcompensate in an attempt to limit the withdrawing force, analogous to pulling a cork from a wine bottle, causing the needle to rebound back toward the port. This situation creates a substantial risk that the caregiver will suffer a needle puncture because the caregiver's hand is necessarily still in the field on the skin surface overlaying the port. Therefore, there is a need for a needle extracting device which substantially reduces the risk of an accidental needle puncture.

SUMMARY OF THE INVENTION

In accordance with the present invention, a needle extractor is provided for safely removing a right angle needle assembly from a port positioned below a patient's skin. The extractor substantially reduces the risk of an accidental needle puncture by eliminating the need for a caregiver to introduce a hand into the field of the needle/port interface.

According to one aspect of the present invention, the needle extractor comprises first and second blades coupled at a pivot in a scissor-like fashion. The first blade is used to engage and extract the needle portion without deforming the needle portion. The first blade has a support portion for supporting the shank portion of the needle assembly. The first blade also has a slot for engaging the needle portion of the needle assembly.

The second blade of the extractor is used to contact a skin surface overlaying the port in order to secure the extractor during needle extraction. The second blade has a contact portion for contacting the skin surface. The second blade also has a slot for engaging the needle portion of the needle assembly. The first blade is offset from the second blade at the pivot such that the support portion of the first blade overlaps the contact portion of the second blade. Each blade includes a handle portion for gripping by the caregiver.

In operation, the blades are inserted between the shank portion of the needle assembly and the skin surface such that the first blade is parallel to the second blade and the needle portion of the needle assembly is engaged by the slotted portion of each blade. Pivoting the first blade with respect to the second blade at the pivot extracts the needle assembly from the port.

According to another aspect of the invention, an extractor comprises top and bottom members coupled at a pivot, each member having a handle and a blade. The top blade has a longitudinal channel and a vertically projecting finger which has a notch. The longitudinal channel supports the shank portion of a needle and the notch of the finger receives tubing coupled to the shank portion. The top and bottom blades include a common longitudinal slot for receiving the needle. The channel and finger stabilize the needle assembly for safe needle extraction. The blades include beveled portions which facilitate insertion of the blades between the skin surface and the needle assembly. The top and bottom members include abutting arcuate portions pivotally attached at the pivot.

In an alternate embodiment, the pivot comprises a ball and socket joint wherein one of the ball and socket is defined by one of the members and wherein the other of the ball and socket is formed by the other of the members.

The above and other features of the invention including various novel details of construction and combinations of parts will now be more particularly described with reference to the accompanying drawings and pointed out in the claims. It will be understood that the particular needle extractor embodying the invention is shown by way of illustration only and not as a limitation of the invention. The principles and features of this invention may be employed in varied and numerous embodiments without departing from the scope of the invention.

BRIEF DESCRIPTION OF THE DRAWINGS

FIG. 6 is a side view of a second embodiment of a needle extractor according to the present invention.

FIG. 7 is a plan view of the needle extractor of FIG. 6.

FIG. 8 is a front view of the needle extractor of FIG. 6.

DETAILED DESCRIPTION OF PREFERRED EMBODIMENTS

Figure 1:
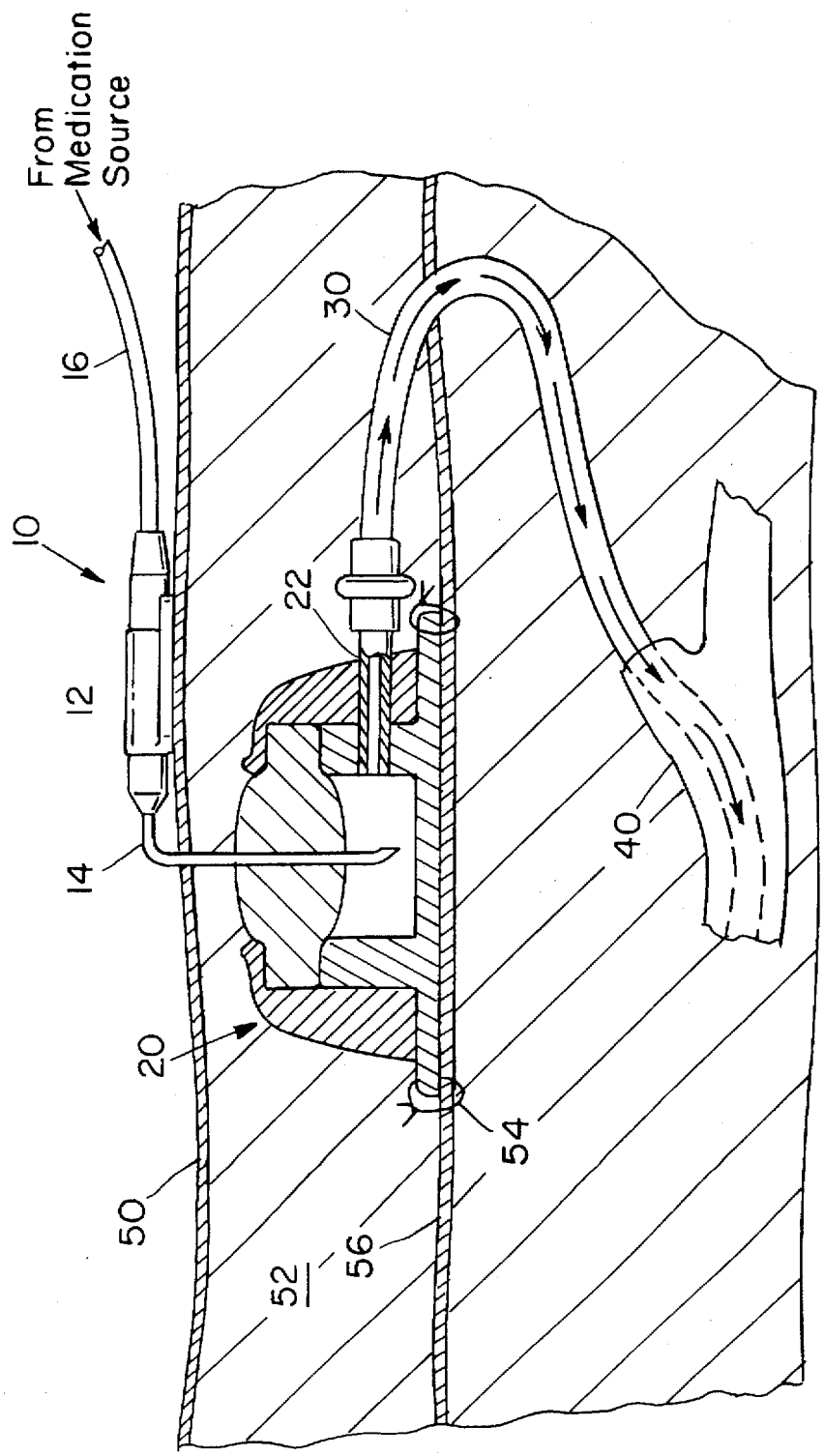
FIG. 1 is a prior art side view of a typical right angle needle assembly inserted into a port.
Figure 2:
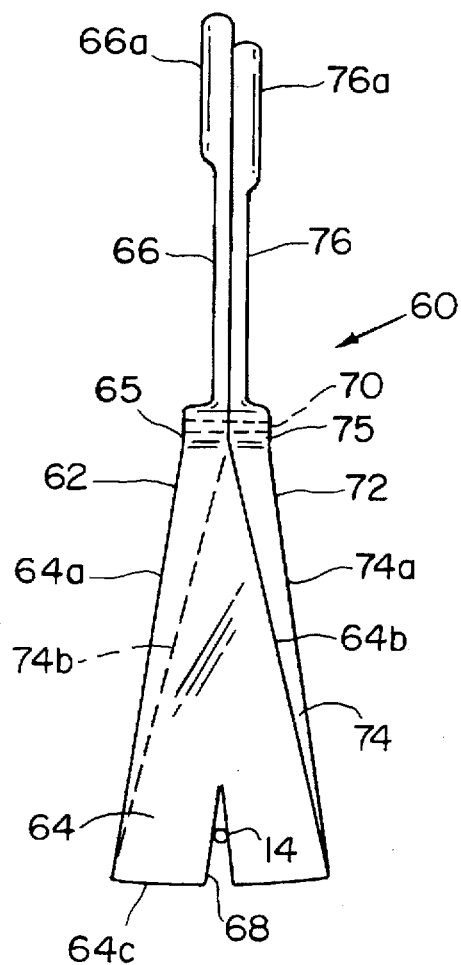
FIG. 2 is a plan view of a first embodiment of a needle extractor according to the present invention.
Figure 3:
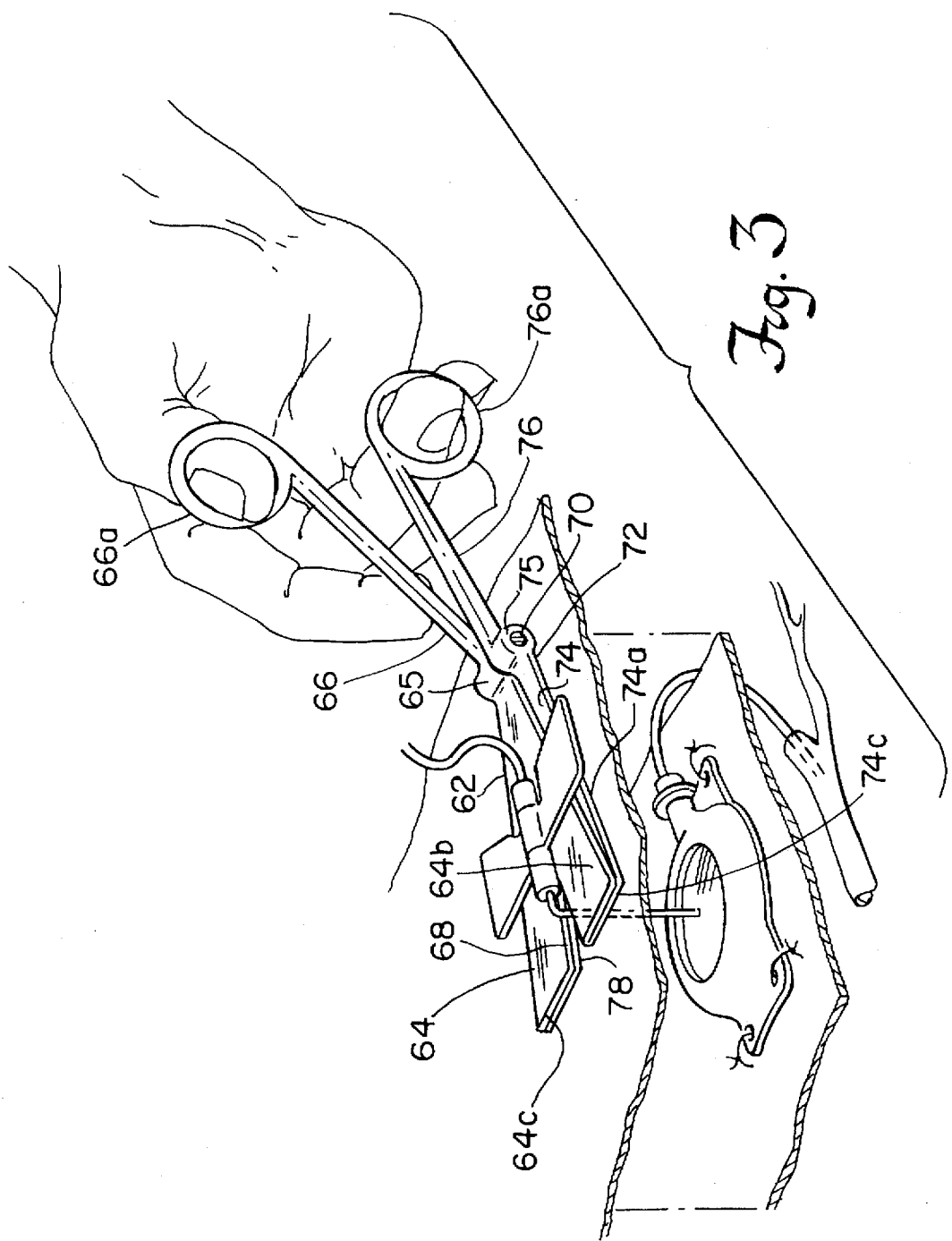
FIG. 3 is a perspective view of the needle extractor of FIG. 2 with its blades inserted between a right angle needle assembly and a patient's skin overlaying the port.

A first embodiment in accordance with the present invention will now be described in detail in connection with FIGS. 2-5. FIG. 2 illustrates a needle extractor 60 having a first blade 62 pivotally attached at pivot pin 70 to a second blade 72. The first blade 62 and the second blade 72 are made of a sterilizable rigid material such as stainless steel or plastic. The first blade 62 comprises a substantially flat insertable support portion 64 located at a distal end and a first handle portion 66 located at a proximate end. The support portion 64 is integrally formed with the first handle portion 66. The support portion 64 functions as a surface which supports a shank portion 12 of a needle assembly 10 (FIG. 1) during needle extraction.

The second blade 72 comprises a substantially flat insertable contact portion 74 located at a distal end and a second handle portion 76 located at a proximate end. The contact portion 74 is integrally formed with the second handle portion 76. The undersurface of contact portion 74 functions as a surface which is brought into contact with a patient's skin surface 50 (FIG. 1) during needle extraction. A first slot 68 formed at the distal end of support portion 64 is aligned with a second slot 78 (FIG. 3) formed at the distal end of contact portion 74. The first slot 68 and the second slot 78 are V-shaped for engaging a needle portion 14 of a needle assembly 10 (FIG. 1). The first handle portion 66 has a portion forming a first finger-holding opening 66a. The second handle portion 76 has a portion forming a second finger-holding opening 76a. Preferably the first finger-holding opening 66a and the second finger-holding opening 76a are shaped to accommodate a thumb and middle finger.

The support portion 64 has a first outer edge 64a, a first inner edge 64b, and a first distal edge 64c. The contact portion 74 has a second outer edge 74a, a second inner edge 74b, and a second distal edge 74c. In a closed position (FIG. 3), the support portion 64 of first blade 62 substantially overlaps the contact portion 74 of second blade 72 and is disposed generally parallel thereto. In the closed position, the first distal edge 64c and the second distal edge 74c are aligned. The first inner edge 64b, the second inner edge 74b, and the first and second distal edges 64c, 74c define the area of overlap.

The first blade 62 has a first cylindrical portion 65 having a hole for receiving pivot pin 70 located intermediate the support portion 64 and the first handle portion 66. The second blade 72 has a second cylindrical portion 75 having a hole for receiving pivot pin 70 located intermediate the contact portion 74 and the second handle portion 76. The first cylindrical portion 65 and the second cylindrical portion 75 are aligned for receiving the pivot pin 70.

Figure 4:
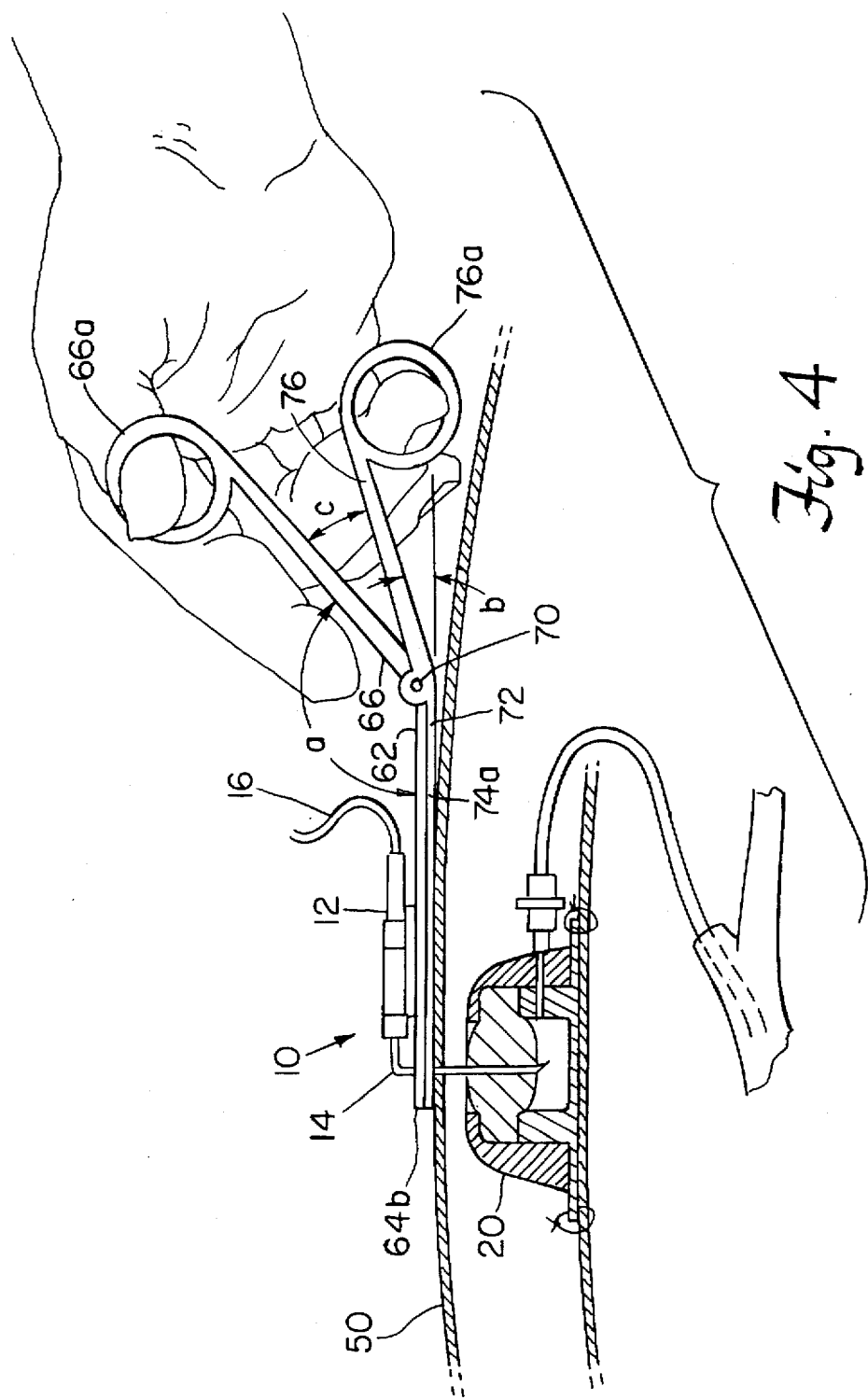
FIG. 4 is a side view of the needle extractor of FIG. 2 with its blades inserted between a right angle needle assembly and a patient's skin overlaying the port.

In the closed position of the extractor 60 shown in FIG. 4, the angle a formed by the support portion 64 and the first handle portion 66 is preferably approximately 120 degrees. The angle b of inclination of the contact portion 74 relative to the second handle portion 76 is preferably approximately 20 degrees. The angle c of inclination of the first handle portion 66 relative to the second handle portion 76 is preferably approximately 40 degrees. The angles a, b, and c are not limited to the values noted above, and may be set to other values so long as the extractor of the present invention can be freely handled as if it were an extension of the hand of the caregiver.

Figure 5:
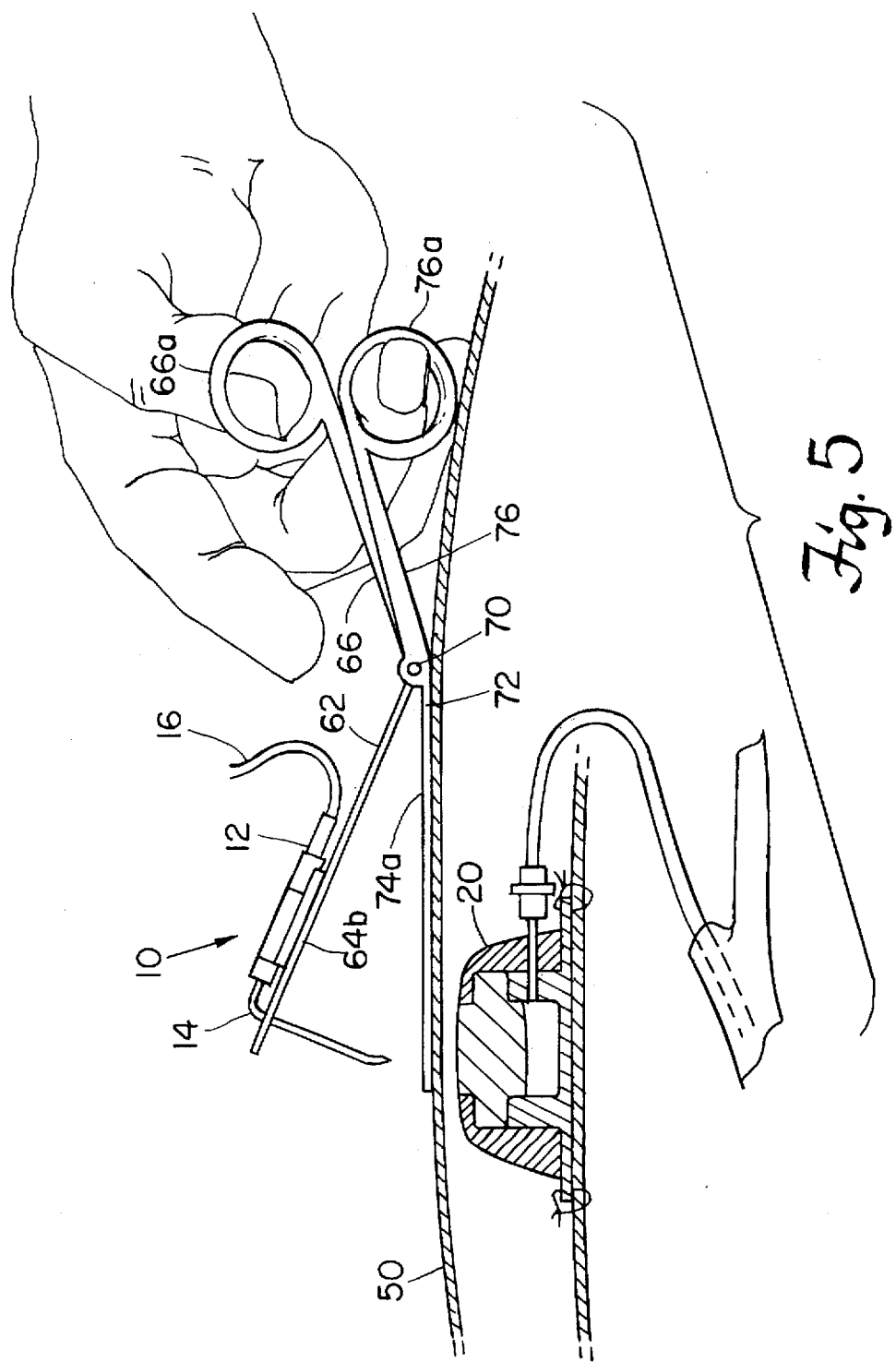
FIG. 5 is a side view of the needle extractor of FIG. 2 after the blades have cooperated to removed a right angle needle assembly.

The utility of the extractor according to the present invention will now be described in detail in connection with FIGS. 4 and 5. In operation, the thumb can be inserted into the first finger-holding opening 66a and the middle finger can be inserted into the second finger-holding opening 76a. Then, the extractor, having the first blade 62 and the second blade 72 disposed in the closed position as shown in FIG. 4, is inserted between a skin surface 50 (overlaying a port 20) and a shank portion 12 of a right angle needle assembly 10 such that the needle portion 14 is engaged in the first slot 68 and the second slot 78. The undersurface of the contact portion 74 of the second blade 72 exerts a downward pressure on the skin surface 50 which secures the extractor against the port 20, thereby eliminating the risk created by the need for the caregiver's hand to be in the field. When the first blade 62 is pivoted about pivot pin 70 relative to the second blade 72 by depressing the first handle portion 66 with respect to the stationary second handle portion 76 in a scissors-like fashion (FIG. 5), the support portion of the first blade 62 exerts an upward pressure on the shank portion 12 which extracts the needle portion 14 from the port 20 without deforming the needle portion 14. The extracted needle portion 14 remains engaged in the slot 68 such that it may be disposed of without causing any further risk to the caregiver.

Referring now to FIGS. 6-9, a second embodiment in accordance with the present invention is shown. A needle extractor 90 includes a top member 92 having a top handle 102 integrally formed with a top blade 106 at an obtuse angle and a bottom member 94 having a bottom handle 104 integrally formed with a bottom blade 108. The bottom blade 108 and the bottom handle 104 are also formed at an obtuse angle. The extractor 90 is preferably made of plastic such as polypropylene. The top and bottom handles 102, 104 have arcuate finger-holding surfaces 102a, 104a respectively. In this embodiment, the finger-holding surfaces 102a, 104a can more readily accommodate different sized fingers and various finger grasping configurations.

Figures 9, 10:
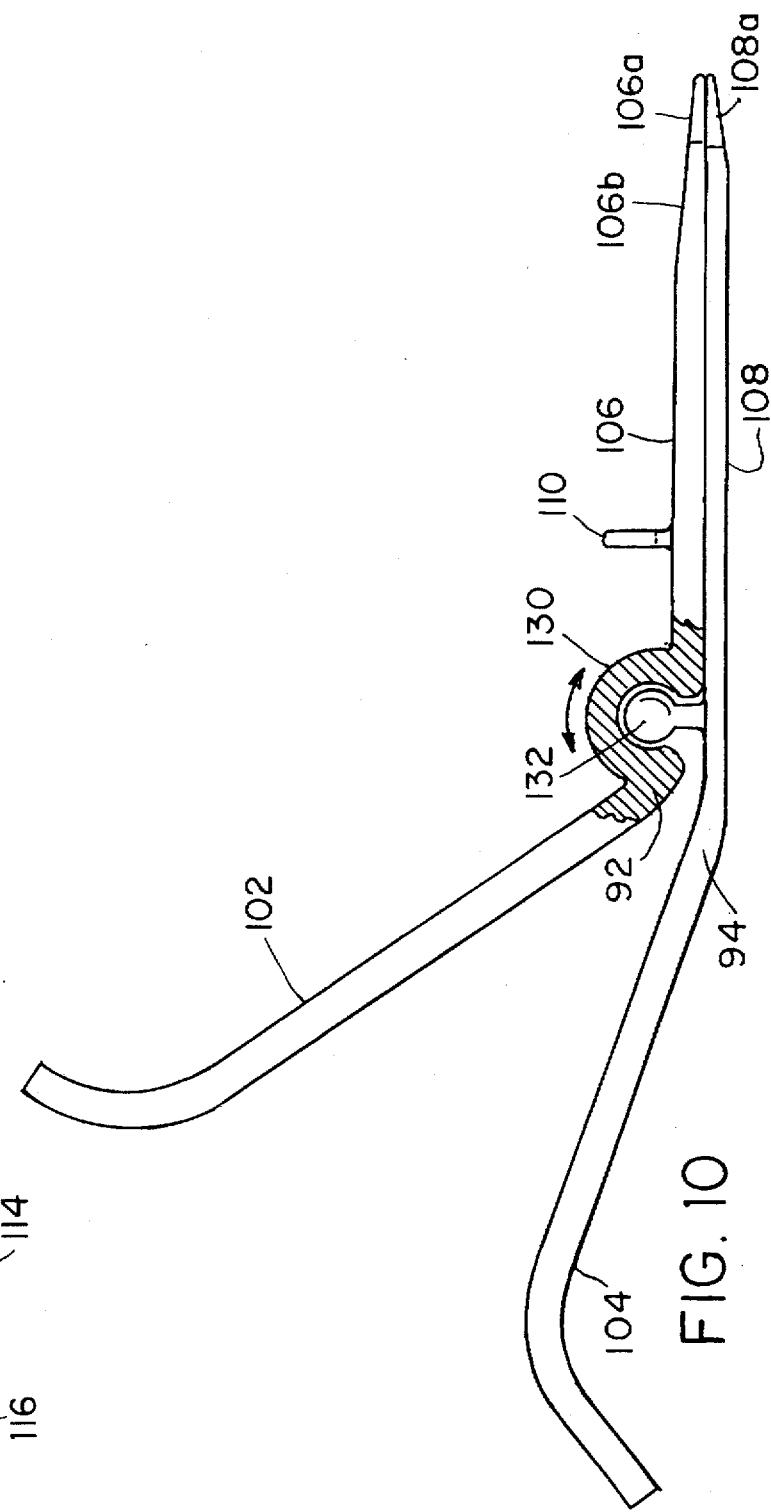
FIG. 9 is a sectional view of the needle extractor of FIG. 7 taken along line D—D.
FIG. 10 is a partial side view of a ball and socket pivot arrangement in another embodiment.

The top and bottom members 92, 94 include intermediate abutting arcuate portions 114, 116 respectively that are pivotally attached at pivot pin 112 (FIG. 9). The pivot pin 112 is a cylindrical projection from portion 114 which is received in portion 116 and is seated in recessed area 113 which avoids interference with the patient.

The top and bottom blades 106, 108 are substantially flat, parallel and overlapping and include a common longitudinal slot 120 formed therein for receiving a needle portion 14 of a right angle needle assembly 10 (FIG. 1). The blades 106, 108 include opposed beveled portions 106a, 108a which facilitate insertion of the blades between the skin surface 50 and the right angle needle assembly 10 (FIG. 1). The top blade 106 includes a tapered portion 106b adjacent beveled portion 106a that further facilitates insertion.

The top blade 106 has a longitudinal gutter or channel 118 formed therein for positioning and aligning the shank portion 12 of the right angle needle assembly 10 (FIG. 1)

thereon during needle extraction. A finger 110 projecting vertically from the top blade 106 at a proximate end of the channel 118 includes a notch 122 for receiving and retaining tubing 16 coupled to the distal end of the shank portion 12 of the needle assembly 10 (FIG. 1). The notch 122 accommodates different sized tubing 16. The channel 118 and finger 110 provide for a more secure needle extraction by stabilizing the right angle needle assembly 10 after the needle assembly is removed from the patient and thereby further minimizing accidental needle punctures.

The top and bottom handles 102, 104 in a closed position of the extractor 90 are spaced apart at an acute angle d. In the open or operating position, top handle 102 is pivoted towards the bottom handle 104. Movement of the top handle 102 towards the bottom handle 104 causes the top blade 106 to move away from stationary bottom blade 108 to effect extraction of a needle assembly 10 (FIG. 1).

In another embodiment, the pivot pin arrangement shown in FIG. 9 is replaced by a ball and socket pivot arrangement as shown in FIG. 10. In this embodiment, the top member 92 includes a socket portion 130 and the bottom member 94 includes a ball portion 132. The ball and socket mechanism 130, 132 eliminates the need for a pivot pin and provides for a two-piece, snap-fit construction leading to less expensive manufacturing cost.

Equivalents

This completes the description of the preferred embodiments of the invention. Those skilled in the art will know, or be able to ascertain using no more than routine experimentation, many equivalents to the specific embodiments of the invention described herein. These and all other equivalents are intended to be encompassed by the following claims.

What is claimed is:

1. An extractor for removing a right angle needle inserted below a skin surface, wherein the needle has a needle portion and an integrally formed shank portion at an angle to the needle portion, the extractor comprising:

a top member comprising a top handle and a top blade, the top blade having a top slot and an elongate longitudinal channel aligned with the top slot longitudinally of the top blade for supporting the shank portion while the slot engages the needle portion;

a bottom member comprising a bottom handle and a substantially planar bottom blade having a bottom slot alignable with the top slot;

wherein the top and bottom members are coupled at a pivot and when pivoted the top slot aligns with the bottom slot for receiving the needle portion.

2. The extractor of claim 1 wherein the top member further comprises a finger projecting vertically from the top blade, the finger having a notch for receiving tubing coupled to the shank portion of the needle.

3. The extractor of claim 1 wherein the top and bottom blades are flat and include beveled end portions.

4. The extractor of claim 1 wherein the top and bottom members include abutting arcuate portions pivotally attached at the pivot.

5. The extractor of claim 1 wherein the top and bottom handles have arcuate finger-holding surfaces.

6. The extractor of claim 1 wherein the pivot is recessed.

7. The extractor of claim 1 wherein the pivot comprises a ball and socket joint wherein one of the ball and socket of the ball and socket joint is defined by one of the members and wherein the other of the ball and socket of the ball and socket joint is formed by the other of the members.

8. The extractor of claim 1 wherein the top and bottom handles in a closed position of the extractor are spaced apart at an angle.

9. The extractor of claim 1 wherein the extractor is formed of plastic.

10. An extractor for removing a right angle needle inserted below a skin surface, wherein the needle has a needle portion and an integrally formed shank portion at an angle to the needle portion, the extractor comprising:

a top member comprising a top handle and a top blade, the top blade having a proximate end and a distal end, a top slot at the distal end and a finger projecting from the top member adjacent the proximate end of the top blade and substantially perpendicular thereto, the finger having a retaining notch for retaining tubing coupled to the shank portion of the needle; and a bottom member comprising a bottom handle and a bottom blade having a bottom slot alignable with the top slot;

wherein the top and bottom members are coupled at a pivot and when pivoted the top slot aligns with the bottom slot for receiving the needle portion.

11. The extractor of claim 10 wherein the top blade includes a longitudinal channel for supporting the shank portion of the needle.

12. The extractor of claim 10 wherein the top and bottom blades are flat and include beveled end portions.

13. The extractor of claim 10 wherein the top and bottom members include abutting arcuate portions pivotally attached at the pivot.

14. The extractor of claim 10 wherein the pivot comprises a ball and socket joint wherein one of the ball and socket of the ball and socket joint is defined by one of the members and wherein the other of the ball and socket of the ball and socket joint is formed by the other of the members.

15. A needle extractor comprising:

a top member having a top blade, the top blade having a top slot at a distal end of the blade and a longitudinal channel aligned with the top slot longitudinally of the top blade;

a retaining member projecting adjacent from a proximate end of the top blade and substantially perpendicular thereto, the retaining member having a notch aligned with the channel and the top slot; and a bottom member having a bottom blade including a bottom slot alignable with the top slot;

wherein the top and bottom members are coupled at a pivot and when pivoted the top slot aligns with the bottom slot.

16. The needle extractor of claim 15 wherein the top and bottom blades are flat and include beveled end portions.

17. The needle extractor of claim 15 wherein the top and bottom members include abutting arcuate portions pivotally attached at the pivot.

18. The needle extractor of claim 15 wherein the pivot comprises a ball and socket joint wherein one of the ball and socket of the ball and socket joint is defined by one of the members and wherein the other of the ball and socket of the ball and socket joint is formed by the other of the members.

19. An extractor for removing a right angle needle inserted below a skin surface, wherein the needle has a needle portion and an integrally formed shank portion at an angle to the needle portion, the extractor comprising:

a first blade including a first slot at a distal end of the blade for engaging the needle portion, and a support portion for supporting the shank portion of the needle;

a retaining member projecting adjacent from a proximate end of the first blade and substantially perpendicular thereto; the retainer member having a notch aligned with the first slot;

a second blade including a second slot for engaging the needle portion, and a substantially flat insertable contact portion for contacting the skin surface; and a pivot coupled to the first and second blades; the support portion and the contact portion being disposed generally parallel to each other and substantially overlapping, and the slots being aligned in a closed position such that when the support portion and the contact portion of the extractor are inserted between the shank portion of the needle and the skin surface to engage the needle portion in the first and second slots, and the first blade is pivoted with respect to the second blade, the needle is removed.

20. The extractor of claim 19 wherein the blades include beveled end portions.

* * * * *